(12) United States Patent
Bian et al.

(10) Patent No.: US 10,472,389 B2
(45) Date of Patent: Nov. 12, 2019

(54) METHODS OF INCREASING PROTEIN PURITY USING PROTEIN A BASED CHROMATOGRAPHY

(71) Applicant: EMD Millipore Corporation, Burlington, MA (US)

(72) Inventors: Nanying Bian, Lexington, MA (US); Melissa Holstein, Concord, MA (US)

(73) Assignee: EMD Millipore Corporation, Burlington, MA (US)

( * ) Notice: Subject to any disclaimer, the term of this patent is extended or adjusted under 35 U.S.C. 154(b) by 392 days.

(21) Appl. No.: 14/768,254

(22) PCT Filed: Mar. 7, 2014

(86) PCT No.: PCT/US2014/021802
§ 371 (c)(1),
(2) Date: Aug. 17, 2015

(87) PCT Pub. No.: WO2014/159064
PCT Pub. Date: Oct. 2, 2014

(65) Prior Publication Data
US 2016/0122385 A1    May 5, 2016

Related U.S. Application Data

(60) Provisional application No. 61/783,381, filed on Mar. 14, 2013.

(51) Int. Cl.
| | | |
|---|---|---|
| *C07K 1/22* | (2006.01) | |
| *C07K 16/06* | (2006.01) | |
| *B01D 15/16* | (2006.01) | |
| *B01D 15/38* | (2006.01) | |
| *C07K 1/36* | (2006.01) | |

(52) U.S. Cl.
CPC .............. *C07K 1/22* (2013.01); *B01D 15/168* (2013.01); *B01D 15/3809* (2013.01); *C07K 1/36* (2013.01); *C07K 16/065* (2013.01)

(58) Field of Classification Search
None
See application file for complete search history.

(56) References Cited

U.S. PATENT DOCUMENTS

| | | | |
|---|---|---|---|
| 6,339,142 B1 | 1/2002 | Basey et al. | |
| 6,417,335 B1 | 7/2002 | Basey et al. | |
| 6,620,918 B2 | 9/2003 | Ansaldi et al. | |
| 8,329,860 B2 * | 12/2012 | Hall | B01D 15/3809 530/324 |
| 8,754,196 B2 * | 6/2014 | Spector | B01D 15/3809 530/402 |
| 9,657,055 B2 * | 5/2017 | Johansson | B01J 20/3274 |
| 2002/0010319 A1 | 1/2002 | Ansaldi et al. | |
| 2003/0078388 A1 | 4/2003 | Basey et al. | |
| 2006/0257972 A1 * | 11/2006 | Ishihara | C07K 16/065 435/69.1 |
| 2008/0167450 A1 * | 7/2008 | Pan | C07K 1/22 530/387.3 |
| 2010/0048876 A1 * | 2/2010 | Hall | B01D 15/3809 530/387.1 |
| 2010/0069617 A1 | 3/2010 | Gagnon | |
| 2010/0168395 A1 * | 7/2010 | Sato | C07K 1/22 530/387.3 |
| 2010/0221844 A1 * | 9/2010 | Bian | B01D 15/3809 436/501 |
| 2010/0331527 A1 * | 12/2010 | Davis | C07K 16/2809 530/387.3 |
| 2012/0208234 A1 * | 8/2012 | Yoshida | B01J 20/286 435/69.1 |
| 2013/0046056 A1 * | 2/2013 | Spector | B01D 15/3809 525/54.1 |
| 2014/0329995 A1 * | 11/2014 | Johansson | B01J 20/3274 530/387.9 |
| 2017/0247407 A1 * | 8/2017 | Johansson | B01J 20/3274 |

FOREIGN PATENT DOCUMENTS

| | | | | |
|---|---|---|---|---|
| CN | 102686738 A | 9/2012 | | |
| JP | 2012-254981 A | 12/2012 | | |
| JP | 2013-503877 A | 2/2013 | | |
| WO | 1999/062936 A1 | 12/1999 | | |
| WO | WO-2008039141 A1 * | 4/2008 | ......... | B01D 15/3809 |
| WO | 2011/028753 A1 | 3/2011 | | |
| WO | 2012/123488 A1 | 9/2012 | | |
| WO | 2013/109302 A2 | 7/2013 | | |
| WO | 2014/159064 A1 | 10/2014 | | |

OTHER PUBLICATIONS

Zamolo et al. "Experimental and thoretical investigation of effect of spacer arm and support matrix of synthetic affinity chromatographic materials for the purificaiton of monoclonal antibodies" J. Phys. Chem. B, 114, 9367-9380 (Year: 2010).*

International Search Report received for PCT Patent Application No. PCT/US2014/021802, dated Jul. 29, 2014, 3 pages.

(Continued)

*Primary Examiner* — Daniel E Kolker
*Assistant Examiner* — James L Rogers
(74) *Attorney, Agent, or Firm* — EMD Millipore Corporation

(57) ABSTRACT

The present invention provides methods for increasing purity of an Fc-containing protein by removing protein aggregates during the Protein A chromatography step used during the purification of the Fc-containing protein.

21 Claims, 7 Drawing Sheets

Specification includes a Sequence Listing.

(56) References Cited

OTHER PUBLICATIONS

Pan et al., "Quantitation of Soluble Aggregates in Recombinant Monoclonal Antibody Cell Culture by pH-gradient Protein A Chromatography", Analytical Biochemistry, vol. 388, No. 2, 2009, pp. 273-278.

International Preliminary Report on Patentability received for PCT Patent Application No. PCT/US2014/021802, dated Sep. 24, 2015, 10 pages.

* cited by examiner

SEQUENCE LISTING

```
<160> NUMBER OF SEQ ID NOS: 4

<210> SEQ ID NO 1
<211> LENGTH: 58
<212> TYPE: PRT
<213> ORGANISM: Staphylococcus aureus

<400> SEQUENCE: 1

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 2
<211> LENGTH: 174
<212> TYPE: DNA
<213> ORGANISM: Staphylococcus aureus

<400> SEQUENCE: 2
gcggataaca aattcaacaa ggagcaacag aacgcattct atgaaattct gcacctgccg      60
aatctgacgg aggagcaacg taacggcttt atccagtccc tgaaggatga tccgtctgtg     120
tctaaagaga tcctggcgga ggcaaaaaaa ctgaatgatg cacaagctcc gaaa           174

<210> SEQ ID NO 3
<211> LENGTH: 290
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Lys Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys Ala Asp Asn Lys Phe Asn
    50                  55                  60
```

```
Lys Glu Gln Gln Asn Ala Phe Tyr Glu Ile Leu His Leu Pro Asn Leu
 65                  70                  75                  80

Thr Glu Glu Gln Arg Asn Lys Phe Ile Gln Ser Leu Lys Asp Asp Pro
                 85                  90                  95

Ser Val Ser Lys Glu Ile Leu Ala Glu Ala Lys Lys Leu Asn Asp Ala
            100                 105                 110

Gln Ala Pro Lys Ala Asp Asn Lys Phe Asn Lys Glu Gln Gln Asn Ala
        115                 120                 125

Phe Tyr Glu Ile Leu His Leu Pro Asn Leu Thr Glu Glu Gln Arg Asn
130                 135                 140

Lys Phe Ile Gln Ser Leu Lys Asp Asp Pro Ser Val Ser Lys Glu Ile
145                 150                 155                 160

Leu Ala Glu Ala Lys Lys Leu Asn Asp Ala Gln Ala Pro Lys Ala Asp
                165                 170                 175

Asn Lys Phe Asn Lys Glu Gln Gln Asn Ala Phe Tyr Glu Ile Leu His
            180                 185                 190

Leu Pro Asn Leu Thr Glu Glu Gln Arg Asn Lys Phe Ile Gln Ser Leu
        195                 200                 205

Lys Asp Asp Pro Ser Val Ser Lys Glu Ile Leu Ala Glu Ala Lys Lys
210                 215                 220

Leu Asn Asp Ala Gln Ala Pro Lys Ala Asp Asn Lys Phe Asn Lys Glu
225                 230                 235                 240

Gln Gln Asn Ala Phe Tyr Glu Ile Leu His Leu Pro Asn Leu Thr Glu
                245                 250                 255

Glu Gln Arg Asn Lys Phe Ile Gln Ser Leu Lys Asp Asp Pro Ser Val
            260                 265                 270

Ser Lys Glu Ile Leu Ala Glu Ala Lys Lys Leu Asn Asp Ala Gln Ala
        275                 280                 285

Pro Lys
    290

<210> SEQ ID NO 4
<211> LENGTH: 271
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ala Phe Asn Lys Glu Gln Gln Asn Ala Phe Tyr Glu Ile Leu His Leu
  1               5                  10                  15

Pro Asn Leu Thr Glu Glu Gln Arg Asn Lys Phe Ile Gln Ser Leu Lys
             20                  25                  30

Asp Asp Pro Ser Val Ser Lys Glu Ile Leu Ala Glu Ala Lys Lys Leu
         35                  40                  45

Asn Asp Ala Gln Ala Pro Lys Phe Asn Lys Glu Gln Gln Asn Ala Phe
     50                  55                  60

Tyr Glu Ile Leu His Leu Pro Asn Leu Thr Glu Glu Gln Arg Asn Lys
 65                  70                  75                  80

Phe Ile Gln Ser Leu Lys Asp Asp Pro Ser Val Ser Lys Glu Ile Leu
                 85                  90                  95

Ala Glu Ala Lys Lys Leu Asn Asp Ala Gln Ala Pro Lys Phe Asn Lys
            100                 105                 110

Glu Gln Gln Asn Ala Phe Tyr Glu Ile Leu His Leu Pro Asn Leu Thr
```

-continued

```
             115                 120                 125
Glu Glu Gln Arg Asn Lys Phe Ile Gln Ser Leu Lys Asp Asp Pro Ser
         130                 135                 140
Val Ser Lys Glu Ile Leu Ala Glu Ala Lys Lys Leu Asn Asp Ala Gln
145                 150                 155                 160
Ala Pro Lys Phe Asn Lys Glu Gln Gln Asn Ala Phe Tyr Glu Ile Leu
                 165                 170                 175
His Leu Pro Asn Leu Thr Glu Glu Gln Arg Asn Lys Phe Ile Gln Ser
             180                 185                 190
Leu Lys Asp Asp Pro Ser Val Ser Lys Glu Ile Leu Ala Glu Ala Lys
         195                 200                 205
Lys Leu Asn Asp Ala Gln Ala Pro Lys Phe Asn Lys Glu Gln Gln Asn
     210                 215                 220
Ala Phe Tyr Glu Ile Leu His Leu Pro Asn Leu Thr Glu Glu Gln Arg
225                 230                 235                 240
Asn Lys Phe Ile Gln Ser Leu Lys Asp Asp Pro Ser Val Ser Lys Glu
                 245                 250                 255
Ile Leu Ala Glu Ala Lys Lys Leu Asn Asp Ala Gln Ala Pro Lys
             260                 265                 270
```

METHODS OF INCREASING PROTEIN PURITY USING PROTEIN A BASED CHROMATOGRAPHY

SEQUENCE LISTING

The instant application contains a Sequence Listing which has been submitted electronically in ASCII format and is hereby incorporated by reference in its entirety. Said ASCII copy, created on Dec. 9, 2015, is named P13-034US_SL.txt and is 6,328 bytes in size.

FIELD OF THE INVENTION

The present invention provides methods for increasing purity of an Fc-containing protein by reducing the level of protein aggregates in a sample using Protein A based chromatography which employs Protein A ligands based on the C domain of Protein A.

BACKGROUND OF THE INVENTION

Conventional processes for protein purification typically involve cell culture methods, e.g., using either mammalian or bacterial cell lines recombinantly engineered to produce the protein of interest followed by: (a) a clarification step for the removal of cells and cellular debris, e.g., using differential centrifugation and/or filtration; and (b) one or more downstream chromatography steps to separate the protein of interest from various impurities in the clarified cell culture feed.

Protein aggregates or high molecular weight protein species are one of the important impurities that need to be removed from biopharmaceutical preparations containing a product of interest, e.g., an Fc-containing protein or an antibody molecule. For example, protein aggregates and other contaminants must be removed from biopharmaceutical preparations containing a product of interest before the product can be used in diagnostic, therapeutic or other applications. This is especially important in case of therapeutic applications and for obtaining Food and Drug Administration approval.

In case of monoclonal antibodies and Fc-containing proteins, the industry standard for purification processes typically involves a purification process, which includes several steps. One of the important steps is a purification step which employs an affinity ligand called Protein A, isolated from *Staphylococcus aureus*, and which binds the Fc-region of antibodies. Typically, protein aggregates also bind the Protein A column, and often end up in the same elution pool as the Fc-containing protein.

Removal of protein aggregates can be challenging as often there are similarities between the physical and chemical properties of protein aggregates and the product of interest in a biopharmaceutical preparation, which generally is a monomeric molecule. In case of Fc-containing proteins, following Protein A chromatography, one or more different methods may be used downstream for the removal of protein aggregates from biopharmaceutical preparations including, for example, size exclusion chromatography, ion exchange chromatography and hydrophobic interaction chromatography.

Previously it has been reported that some of the protein aggregates can be removed during the Protein A chromatography step by using pH gradient elution. See, e.g., PCT Publication No. WO2011/028753 and Pan et al., Analytical Biochemistry 388 (2009) 273-278, incorporated by reference herein. However, as discussed in these references, the protein aggregates are eluted off of the Protein A column after or with the elution of the Fc-containing protein.

SUMMARY OF THE INVENTION

The present invention provides novel and improved methods for removing a greater amount of protein aggregates from a sample containing an Fc-containing protein relative to the methods described previously. The methods described herein employ a Protein A ligand based on the C domain of Protein A and use either pH gradient elution or pH step elution, resulting in the elution of at least 30% of the protein aggregates prior to the elution of the Fc-containing protein, in addition to removal of protein aggregates after the elution of the Fc-containing protein. Consequently, the methods described herein result in an overall greater removal of protein aggregates relative to the methods described in the prior art, which primarily remove protein aggregates after the elution of the Fc-containing protein.

The present invention is based, at least in part, on the novel and unexpected discovery that by binding an Fc-containing protein to an immobilized Protein A ligand based on the C domain of Protein A, and eluting using a pH gradient method or a pH step method, as described herein, that at least 30% of the protein aggregates are removed prior to the elution of the Fc-containing protein, in addition to removal of the protein aggregates following the elution of the Fc-containing protein. The removal of a greater amount of protein aggregates than the prior art methods not only results in an increased purity of the Fc-containing protein in the elution pool, but also reduces the burden of one or more additional downstream steps that may be used to removed such protein aggregates. In some embodiments, the methods described herein reduce the number of downstream steps to remove protein aggregates or obviate the need to use one or more downstream steps to remove protein aggregates from the elution pool following the Protein A step.

In some embodiments, a method of reducing the level of protein aggregates in an elution pool containing an Fc-containing protein is provided, the method comprising the steps of: providing a sample comprising an Fc-containing protein and protein aggregates; contacting the sample with a protein A ligand immobilized onto a solid support, wherein the protein A ligand is based on the C domain of Protein A, such that the Fc-region containing protein binds to the protein A ligand; obtaining an elution pool containing the Fc-containing protein using a pH gradient method employing a high pH buffer and a low pH buffer; wherein at least 30% of the protein aggregates are removed prior to the elution of the Fc-containing protein in addition to protein aggregates that are removed after the elution of the Fc-containing protein, thereby reducing the level of protein aggregates in the elution pool.

In some embodiments, a method of reducing the level of protein aggregates in an elution pool containing an Fc-containing protein is provided, the method comprising the steps of: providing a sample comprising an Fc-containing protein and protein aggregates; contacting the sample with a protein A ligand immobilized onto a solid support, wherein the protein A ligand is based on the C domain of Protein A, such that the Fc-region containing protein binds to the protein A ligand; obtaining an elution pool containing the Fc-containing protein using a pH step method employing two or more buffers used sequentially in the order of descending pH values, wherein at least 30% of the protein aggregates are removed prior to the elution of the Fc-containing protein in addition to protein aggregates that are removed after the elution of the Fc-containing protein, thereby reducing the level of protein aggregates in the elution pool.

In some embodiments, an elution pool is obtained using a pH step method which employs a series of small pH change steps, in descending order of pH values. In some embodiments, each small pH change is in the order of 0.1 to 0.5. In a particular embodiment, each small pH change is in the order of 0.2.

In some embodiments, the series of small pH change steps include two or more steps, or three or more steps, or four or more steps, or five or more steps, or six or more steps, or seven or more steps, or eight or more steps, or nine or more steps, or ten or more steps. In a particular embodiment, the series of pH change steps which are used are in the order of: pH 5.0; pH 4.8; pH 4.6; pH 4.4; pH 4.2; pH 4.0; pH 3.8; pH 3.6; pH 3.4; pH 3.2; and pH 3.0.

In some embodiments according to the present invention, a method for increasing the purity of an Fc-containing protein is provided, the method comprising the steps of: providing a sample comprising an Fc-containing protein and protein aggregates; contacting the sample with a Protein A ligand immobilized onto a solid support, wherein the Protein A ligand is based on the C domain of Protein A, and wherein the Fc-containing protein binds to the Protein A ligand; and obtaining an elution pool containing the Fc-containing protein using a pH gradient elution method or a pH step method, wherein at least 30% of the protein aggregates are removed prior to elution of the Fc-containing protein in addition to protein aggregates that are removed after the elution of the Fc-containing protein, thereby increasing the purity of the Fc-containing protein in the elution pool.

In some embodiments, the Protein A comprises the amino acid sequence set forth in SEQ ID NO:3. In other embodiments, the Protein A comprises the amino acid sequence set forth in SEQ ID NO:4.

The some embodiments of the methods described herein, in case of the pH gradient method of elution, a high pH buffer has a pH of about 6.0 and the low pH buffer has a pH of about 3.0.

In some embodiments of the methods described herein, in case of the pH step method of elution, at least one of the buffers used has a pH ranging from 3.6 to 4.4.

In some embodiments, the step elution methods described herein employ a series of small pH change steps, where the pH steps range from a high pH of about 5.0 to a low pH of about 3.0, with each pH step differing from the previous pH step by a pH of 0.1, 0.2, 0.3, 0.4 or 0.5. In a particular embodiment, small pH change steps are used in the order of: 5.0; 4.8; 4.6; 4.4; 4.2; 4.0; 3.8; 3.6; 3.4; 3.2; and 3.0.

In some embodiments, the Fc-containing protein is an antibody or an Fc-fusion protein. In some embodiments, the antibody is a monoclonal antibody.

In some embodiments, in case of pH gradient elution, the pH gradient spans 5 column volumes to 30 column volumes.

Exemplary solid supports used for immobilization of Protein A include, but are not limited to, controlled pore glass, silica, zirconium oxide, titanium oxide, agarose, polymethacrylate, polyacrylate, polyacrylamide, polyvinylether, polyvinyl alcohol and polystyrene and derivatives thereof.

BRIEF DESCRIPTION OF THE DRAWINGS

FIG. 6a depicts a chromatogram for elution of mAb-3 using a series of small pH change steps, where the X-axis represents column volumes (CVs), the left Y-axis is UV 280 absorbance (measured in mAU) and the right Y-axis is pH, where the small pH change steps are: pH 5.0; pH 4.8; pH 4.6; pH 4.4; pH 4.2; pH 4.0; pH 3.8; pH 3.6; pH 3.4; pH 3.2 and pH 3.0. FIG. 6b depicts a zoomed-in version of the major elution peak in the chromatogram in FIG. 6a, showing the percent aggregate species present in each step elution fraction.

DETAILED DESCRIPTION OF THE INVENTION

Figure 1A:
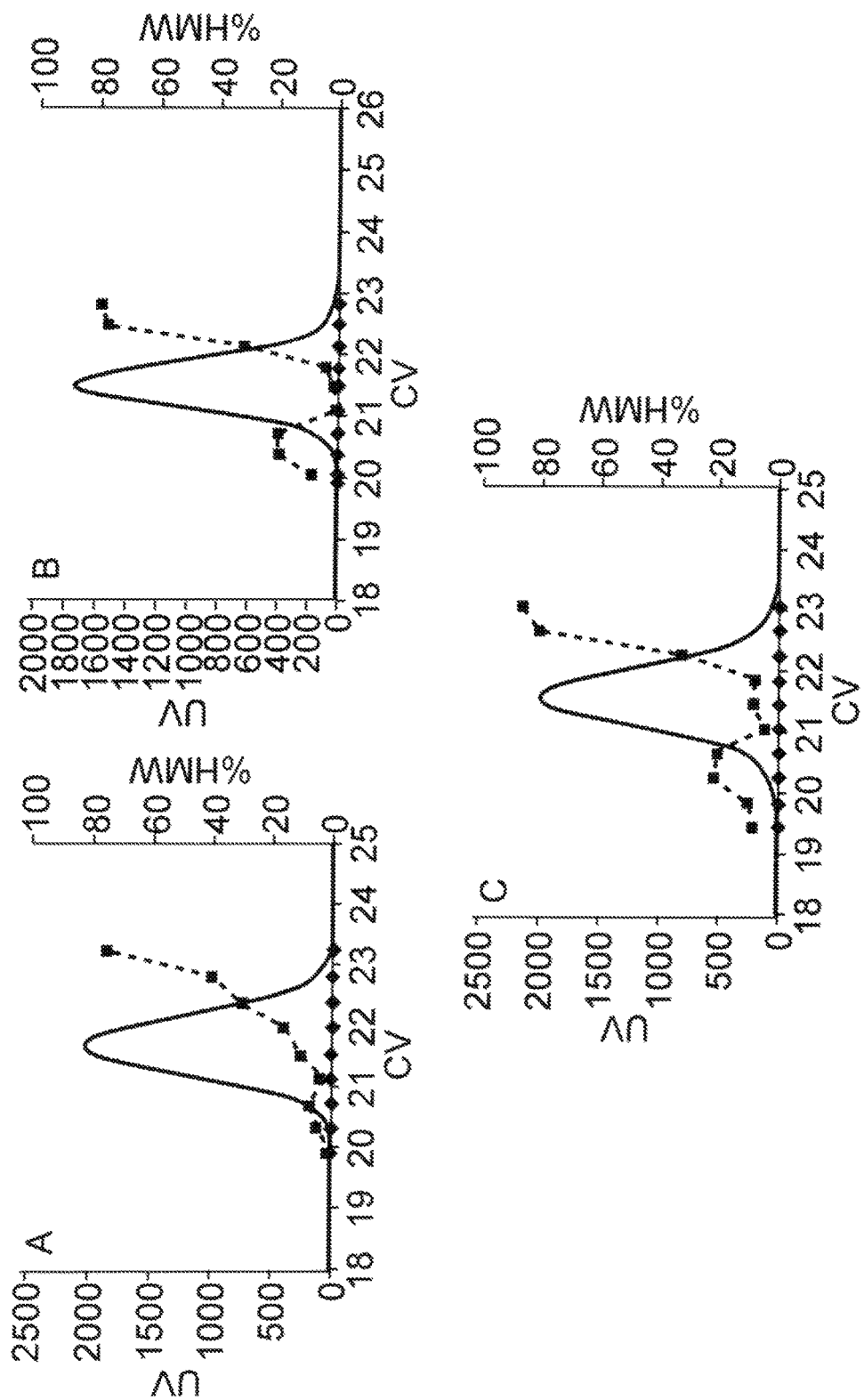
FIG. 1A depicts the elution region of chromatograms for mAb-1 (loading density 12 mg/mL) with pH gradient elution from three resins (A-MabSelect Sure™; B-Resin A and C-Resin C), where the X-axis represents column volumes (CVs), the left Y-axis is UV 280 absorbance (mAU, solid line), and the right Y-axis is the percentage of aggregate species in each fraction as determined by SEC (linked squares). The amount of protein aggregates removed at the pre-peak for Resin A and Resin B are significantly higher than those for MabSelect SuRe™, indicating more efficient aggregate species removal at the beginning of the profile. For all three resins, a large population of aggregate species is also obtained in the fractions at the tail end of the elution profile, as also previously reported for MabSelect Sure™.

The present invention is based, at least on the surprising and unexpected discovery that, when elution of the target protein (e.g., an Fc-containing protein) from a Protein A chromatography column is performed, using pH gradient elution or pH step elution, as described herein, that at least 30% of the protein aggregates are removed prior to elution of the target protein in addition to removal of protein aggregates after the elution of the target protein, leading to higher purity of the target protein in the elution pool. Accordingly, in one embodiment of the invention, a method for purifying a target protein is provided, comprising binding the target protein to a Protein A ligand based on the C domain of Protein A and eluting with a pH gradient. In another embodiment of the invention, a method for purifying a target protein is provided, comprising binding the target protein to a Protein A ligand based on the C domain of Protein A and eluting with a pH step method.

In order that the present disclosure may be more readily understood, certain terms are first defined. Additional definitions are set forth throughout the detailed description.

I. Definitions

As used herein, the term "SpA," "Protein A" or "*Staphylococcus aureus* Protein A," refers to a 42 kDa multi-domain protein isolated from the bacterium *Staphylococcus aureus*. SpA is bound to the bacterial cell wall via its carboxy-terminal cell wall binding region, referred to as the X domain. At the amino-terminal region, it includes five immunoglobulin-binding domains, referred to as E, D, A, B, and C (Sjodhal, *Eur J Biochem*. September 78(2):471-90 (1977); Uhlen et al., *J Biol Chem*. February 259(3):1695-702 (1984)). Each of these domains contains approximately 58 amino acid residues, and they share 65-90% amino acid sequence identity.

Each of the E, D, A, B and C domains of SpA possess distinct Ig-binding sites. One site is for Fc (the constant region of IgG class of Ig) and the other is for the Fab portion of certain Ig molecules (the portion of the Ig that is responsible for antigen recognition). It has been reported that each of the domains contains a Fab binding site. The non-Ig binding portion of SpA is located at the C-terminus and is designated the X region or X-domain.

As used interchangeably herein, the terms "C domain," "C domain of SpA," "C domain of Protein A" and "C domain of *Staphylococcus aureus* Protein A," refer to the polypeptide whose amino acid sequence is set forth in SEQ ID NO:1 or that encoded by, e.g., the nucleotide sequence set forth in SEQ ID NO:2. The "C domain" is a 58 amino acid polypeptide that folds into a three-helix bundle structure. It is capable of Fc binding via residues on the surface of helices 1 and 2, or to Fab via residues on the surface of helices 2 and 3. A Protein A ligand based on the C domain, as used in the methods herein, includes the wild-type C domain sequence as well as any variants and derivatives thereof, which bind an Fc-containing protein and result in the greater removal of protein aggregates using the methods described herein.

In various embodiments, a Protein A ligand based on the C domain of Protein A used in the methods described herein comprises the amino acid sequence set forth in SEQ ID NO:3 or SEQ ID NO:4.

The term "chromatography," as used herein, refers to a dynamic separation technique which separates a target protein (e.g., an immunoglobulin or an Fc-containing protein) from other molecules in the mixture and allows it to be isolated. Typically, in a chromatography method, a mobile phase (liquid or gas) transports a sample containing the target molecule of interest across or through a stationary phase (normally solid) medium. Differences in partition or affinity to the stationary phase separate the different molecules while mobile phase carries the different molecules out at different time.

The term "affinity chromatography." as used herein, refers to a mode of chromatography where a target protein (e.g., an Fc-containing protein) to be separated is isolated by its interaction with a molecule (e.g., a Protein A based ligand) which specifically interacts with the target protein. In various embodiments described herein, affinity chromatography involves the addition of a sample containing a target molecule (e.g., an immunoglobulin or an Fc-containing protein) to a solid support which carries on it a ligand based on the C domain of Protein A.

The term "Protein A affinity chromatography," as used herein, refers to the separation or isolation of substances using Protein A or SpA-based ligands based on the C domain of Protein A, such as those described herein, where the SpA or Protein A ligand is immobilized, e.g., on a solid support.

Examples of Protein A affinity chromatography media/resin known in the art include those having the Protein A immobilized onto a controlled pore glass backbone, e.g., PROSEP® A and PROSEP® vA media/resin (EMD MILLIPORE); those having Protein A immobilized onto a polystyrene solid phase, e.g., the POROS® 50A and POROS® MabCapture™ A media/resin (APPLIED BIOSYSTEMS, INC.); and those having Protein A immobilized on an agarose solid support, e.g., rPROTEIN A SEPHAROSE FAST FLOW™ or MABSELECT™ media or resins (GE HEALTHCARE). The Protein A ligands used in the methods described herein may be immobilized onto any of the above described solid supports.

In addition to the aforementioned matrices, Protein A may also be immobilized onto a hydrophilic crosslinked polymer. See, e.g., U.S. Pat. No. 7,951,885, incorporated by reference herein in its entirety, which describes exemplary hydrophilic crosslinked polymers. Without wishing to be bound by theory, it is contemplated that the ligands encompassed by the present invention may be immobilized onto hydrophilic crosslinked polymers, such as those described in U.S. Pat. No. 7,951,885.

The term "affinity matrix" or "affinity chromatography matrix," as used interchangeably herein, refers to a solid support onto which an affinity chromatography ligand (e.g., based on the C domain of Protein A) is attached. The ligand is capable of binding to a molecule of interest through affinity interaction (e.g., an immunoglobulin or an Fc-containing protein) which is to be purified or removed from a mixture.

The term "target protein" or "protein of interest," as used interchangeably herein, refers to any protein that can be purified using the C domain of Protein A, or a variant or derivative thereof. In various embodiments, the target protein is an Fc-containing protein such as, e.g., an immunoglobulin of an Fc-fusion protein.

The term "immunoglobulin," "Ig" or "antibody" (used interchangeably herein) refers to a protein having a basic four-polypeptide chain structure consisting of two heavy and two light chains, said chains being stabilized, for example, by interchain disulfide bonds, which has the ability to specifically bind antigen. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by β-pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of antibody light chains are referred to interchangeably as "light chain constant regions", "light chain constant domains". "CL" regions or "CL" domains. The "constant" domains of antibody heavy chains are referred to interchangeably as "heavy chain constant regions", "heavy chain constant domains", "CH" regions or "CH" domains. The "variable" domains of antibody light chains are referred to interchangeably as "light chain variable regions", "light chain variable domains", "VL" regions or "VL" domains. The "variable" domains of antibody heavy chains are referred to interchangeably as "heavy chain variable regions", "heavy chain variable domains", "VH" regions or "VH" domains.

Immunoglobulins or antibodies may be monoclonal or polyclonal and may exist in monomeric or polymeric form, for example, IgM antibodies which exist in pentameric form and/or IgA antibodies which exist in monomeric, dimeric or multimeric form. The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fc and/or Fv fragments.

Methods of the invention can be used to purify any antibody or fragment thereof which can bind to Protein A, including but not limited to, human antibodies, humanized antibodies, chimeric antibodies, or fragments thereof. In some embodiments, antibodies purified using the methods described herein are therapeutic antibodies.

Exemplary therapeutic antibodies include Herceptin™; Rituxan™; Avastin™; Bexxar™; Campath™; Erbitux™; Humira™; Raptiva™; Remicade™; ReoPro™; Prolia®; Xgeva®; Simulect™; Synagis™; Xolair™; Zenapax™; Mylotarg™; and Vectibix™. Exemplary Fc fusion proteins include fusion to soluble forms of receptors or enzymes and variants, derivatives, or analogs thereof, such as, e.g., ENBREL®.

It is understood that the target protein purified using the methods described herein is one which contains an Fc region and therefore is amenable to purification by Protein A. The term "Fc region" or "Fc," as used herein, refers to those amino acid residues of an immunoglobulin molecule which interact with Protein A. The Fc region is the crystallizable tail region of an antibody and interacts with cell surface receptors called Fc receptors.

The term "Fc-binding," "binds to an Fc portion" or "binding to an Fc portion" refers to the ability of an affinity ligand described herein, to bind to the constant part (Fc) of an antibody. In some embodiments, a ligand according to the present invention binds an Fc portion of an antibody (e.g., human IgG1, IgG2 or IgG4) with an affinity of at least $10^{-7}$ M, or at least $10^{-8}$ M, or at least $10^{-9}$ M.

As used herein, the term "fragment(s)" refers to a portion of a full length Fc-containing protein such as, e.g., an immunoglobulin. Examples of fragments include Fab fragments, single-chain antibody molecules, diabodies, linear antibodies, and multispecific antibodies formed from antibody fragments.

The Fc-containing proteins which are purified using the methods described herein may be expressed using any suitable expression system or cell type. In some embodiments, an Fc-containing protein is expressed in a mammalian cell, e.g., CHO or NS0 cells, hybridomas, mouse cells etc. In another embodiment, an Fc-containing protein is expressed using a non-mammalian cell culture (e.g., insect cells, yeast cells, *Escherichia coli*, etc.). Following expression in a cell culture, the insoluble species are typically removed using a clarification method such as, e.g., depth filtration, centrifugation, flocculation/precipitation (e.g., acid precipitation or stimuli-responsive polymer). This clarified cell culture is typically loaded onto a Protein A column to separate the Fc-containing protein from soluble impurities such as host cell proteins, DNA, viruses, or other impurities.

As used herein, the term "purified polypeptide' or "purified protein" is an eluted product from a Protein A affinity step using the pH gradient or pH step methods as described herein. Purified polypeptides/proteins preferably contain mostly polypeptide monomers.

As used herein, the term "unpurified polypeptide," "unpurified protein," or "protein load" is a polypeptide or protein in the loading material or starting material prior to the Protein A affinity purification step.

As used herein, the term "purity of an Fc-containing protein" is defined as the monomeric species of the target protein (i.e., an Fc-containing protein) relative to the total protein eluted off of a Protein A chromatography column, which employs a ligand based on the C domain of Protein A immobilized onto a solid support. Accordingly, the purity can be calculated by the ratio of total monomer to the total protein in the elution pool. The total protein may contain one or more of protein fragments, aggregates, monomeric species of the target protein and the variants thereof. In various methods described herein, the purity of an Fc-containing protein is increased by at least 5%, or at least 10%, or at least 15%, or at least 20%, or at least 25%, or at least 30%, or more, relative to Protein A chromatography methods described in the prior art.

Typically, in case of a Protein A chromatography method described herein, following the loading of the Protein A column with a sample containing the target protein, the target protein is eluted off of the column using a suitable elution buffer, concurrently with measurement of UV absorbance at 280 nm, thereby resulting in an elution profile for the target protein. The elution profile typically includes a pre-peak, a peak and a post-peak. Once elution commences, fractions are collected at predetermined column volumes when the protein absorbance measured at 280 nm reaches a certain level, e.g., 50 mAU or higher and ends when the absorbance at 280 nm reaches, e.g., lower than 50 mAU. The elution fraction or fractions with the high absorbance value are the ones that form the peak and contain the target protein. These can be pooled to generate the elution pool containing the target protein. Such fraction or fractions typically fall within the middle of an elution profile. Whereas, fraction or fractions with lower absorbance, which appear at the beginning or towards the end of the elution profile, are generally discarded because they contain protein aggregates.

As used herein, the term "yield of Fc-containing protein" is defined as the amount of protein collected in the elution pool relative to the total amount of protein eluted off of a Protein A chromatography column. In some embodiments, the elution pool contains fractions starting at an absorbance value of 500 mAU or higher and ending with an absorbance value of 500 mAU or lower.

As used herein, the term "pre-peak" refers to the portion of the elution profile for a protein, which is collected before a specified UV absorbance, and is not included in the elution pool. In some embodiments, the pre-peak refers to the total protein recovered before the absorbance reaches 500 mAU or higher.

As used herein, the term "post-peak" refers to the portion of the elution profile for a protein, which is collected after a specified UV absorbance. In some embodiments, the post-peak refers to the total protein recovered after the absorbance reaches 500 mAU or lower.

The term "protein aggregate" or "protein aggregates," as used interchangeably herein, refers to an association of at least two molecules of a product of interest, e.g., an Fc-containing protein. The association of at least two molecules of a product of interest may arise by any means including, but not limited to, non-covalent interactions such as, e.g., charge-charge, hydrophobic and van der Waals interactions; and covalent interactions such as, e.g., disulfide interaction or nonreducible crosslinking. An aggregate can be a dimer, trimer, tetramer, or a multimer greater than a tetramer, etc. The term "protein aggregates," includes any higher order species of the Fc-containing protein.

Aggregate concentration can be measured in a protein sample using Size Exclusion Chromatography (SEC), a well known and widely accepted method in the art (see, e.g., Gabrielson et al., *J. Pharm. Sci.,* 96, (2007), 268-279). In some embodiments, relative concentrations of species of various molecular weights are measured in the elution fractions using UV absorbance, while the molecular weights of the fractions are determined by performing system calibration following instruction of column manufacturer. Other methods for measuring aggregate concentration include, e.g., gel electrophoresis and light scattering.

As used herein, the term "monomer(s)" refers to a single unit of an Fc-containing protein. For example, in the case of an antibody, a monomer consists of two heavy chains and two light chains; in the case of a one-armed antibody, a monomer consists of one heavy chain and one light chain.

The term "ligand," as used herein, refers to a biological molecule based on the C domain of Protein A which is immobilized on a solid support (e.g., a porous surface) and which is capable of attracting an Fc-containing protein. In some embodiments described herein, the ligand comprises the amino acid sequence set forth in SEQ ID NO:3, or variants, fragments or derivatives thereof. In some other embodiments described herein, the ligand comprises the amino acid sequence set forth in SEQ ID NO:4, or variants, fragments or derivatives thereof.

The term "solid support" refers in general to any material (porous or non porous) to which a ligand is attached. The attachment of ligands to the solid support can either be through a covalent bond, such as in the case of grafting, or through coating, adhesion, adsorption, and similar mechanisms. Examples of solid supports used in the methods and compositions described herein include, but are not limited to, membranes, porous beads, winged or porous fibers, monoliths. Suitable membranes include, but are not limited to, surface modified or unmodified polyvinylidene fluoride (PVDF), polyether sulfone (PES), polyetherether sulfone (PEES), cellulose, nylon, polytetrafluoroethylene (PTFE), ultrahigh molecular weight polyethylene (UPE). Suitable porous beads include, but are not limited to, silica, ceramic, polystyrene, polyacrylate, polymethacrylate, polyvinylether, polyvinyl alcohol, polysaccharide including agarose and cellulose. Suitable winged or porous fibers include, but are not limited to, nylon, cellulose, PES. Suitable monoliths include, but are not limited to, silica, polystyrene, polymethacrylate, and polyacrylate, polyacrylamide, polyvinyl alcohol. In some embodiments, the ligand is immobilized onto a chromatography medium such as, e.g., a porous bead, which is then packed into a chromatography column for use.

The term "load density" or "loading density" is the amount of the sample containing an Fc-containing protein loaded onto a chromatography column per volume of chromatography media. The loading density is measured in g/L. In some embodiments, the sample is loaded with a loading density of 5 g/L, or 10 g/L, or 12 g/L, or 15 g/L, or 20 g/L, or 30 g/L, or 40 g/L or higher.

A "buffer" is a solution that resists changes in pH by the action of its acid-base conjugate components. Various buffers which can be employed depending, for example, on the desired pH of the buffer are described in Buffers. A Guide for the Preparation and Use of Buffers in Biological Systems, Gueffroy, D., Ed. Calbiochem Corporation (1975).

The "equilibration buffer" herein is that used to prepare the solid support (with immobilized Protein A) for loading the target protein.

The "wash buffer" is used herein to refer to the buffer that is passed over the solid support (with immobilized Protein A) following loading and prior to elution of the target protein.

II. Protein A Chromatography

Protein A chromatography is a form of affinity chromatography, most commonly used for the purification of Fc-containing proteins such as, e.g., immunoglobulins or antibodies. Generally, a target protein (e.g., an Fc-containing protein) is expressed in a suitable cell culture and the cell culture feed is subjected to clarification, before loading the clarified feed onto a Protein A chromatography media, e.g., packed in a chromatography column.

Protein A chromatography generally employs a solid support such as, e.g., a porous bead or a resin, having a suitable Protein A ligand immobilized thereon. The Protein A bound solid support is then packed in a chromatography column. The column may first be equilibrated with a suitable equilibration buffer. The clarified feed containing the target protein (e.g., an Fc-containing protein) is then contacted with the solid support in the column by loading the column with a sample containing an Fc-containing protein (e.g., a clarified cell culture feed). Typically, soluble impurities such as host cell proteins and DNA do not bind to the Protein A and hence are removed in the flow-through and diverted to the waste. Subsequently, the bound Fc-containing protein is eluted from the Protein A chromatography column by exposure to a suitable elution buffer. Typical flow rates for elution range from 60 column volumes (CV) per hour to 5 CV per hour. In case of gradient elution, typically elution is conducted over 5 to 60 column volumes.

As described herein, elution of the Fc-containing protein may be conducted using two different methods. In some embodiments, a high pH buffer and low pH buffer are mixed to generate a pH gradient ranging from pH 7.0 to 3.0. In some embodiments, the pH gradient starts at 7.0, or about 6.8, or about 6.6, or about 6.4, or about 6.2, or about 6.0, or about 5.8, or about 5.6, or about 5.4, or about 5.2, or about 5.0, or about 4.8, or about 4.6, or about 4.4, or about 4.2, or about 4.0, and the pH gradient ends at 3.0, or about 3.2, or about 3.4, or about 3.6, or about 3.8.

The eluted protein is collected in fractions of fixed volume for further analysis of monomer versus aggregate content.

In some embodiments, two or more buffers of different pH values are used sequentially in a descending order of pH values in order to elute the Protein A bound Fc-containing protein. In some embodiments, the first buffer used for step elution has a pH of 4.4, or about 4.2, or about 4.0, or about 3.8, or about 3.6; and a second buffer used for step elution has a pH of 3.5, or about 3.4, or about 3.3, or about 3.2, or about 3.1, or about 3.0.

In a specific embodiment, the first buffer has a pH of around 3.75 and the second buffer has a pH of around 3.0. The eluted protein is collected in fractions of fixed volume for further analysis of monomer versus aggregate content.

In some embodiments, step elution is used to elute the Protein A bound Fc-containing protein, where small changes in pH are used for elution of the protein in multiple steps over time. Multiple elution pools can subsequently be combined to recover the FPc-containing protein.

In some embodiments, step elution employs a series of small pH change steps in decreasing order of pH with each pH step differing by a pH value of about 0.1 to about 0.5 from the previous pH step. For example, in some embodiments, the high point of the pH is around 5.0, which is decreased in a step wise manner by pH value ranging from 0.1 to 0.5, with the low point of the pH being around 3.0. In a particular embodiment, the series of small pH change steps include pH values in the order of: 5.0; 4.8; 4.6; 4.4; 4.2; 4.0; 3.8; 3.6; 3.4; 3.2 and 3.0.

Additional buffers may also be used in the processes, which facilitate the binding of the protein to the Protein A ligand. Such buffers will typically have a higher pH than the buffers used for step elution method.

III. Exemplary Buffers Used in the Methods Described Herein

As discussed above, a Protein A chromatography column is typically equilibrated prior to loading the column with the sample containing an Fc-containing protein. In some embodiments, the equilibration buffer used is isotonic and has a pH ranging from 6.0 to 8.0. An exemplary equilibration buffer contains 25 mM Tris, 25 mM NaCl, 5 mM EDTA, at pH 7.1.

Another buffer that is typically employed during Protein A chromatography is a loading buffer. The loading buffer is used to load the mixture of the Fc-containing protein and protein aggregates onto the solid support onto which the Protein A is immobilized. Often, the equilibration and loading buffers are the same.

The Protein A-bound Fc-containing protein is subsequently eluted with an elution buffer. In some embodiments described herein, the elution buffer contains a high pH buffer and a low pH buffer, thereby to form a pH gradient which is formed by adjusting the percentage of the high pH buffer and the low pH buffer in the elution buffer. In some embodiments, the elution buffer has a pH ranging from 7.0 to 3.0 or from 6.0 to 3.0. The pH values as used herein are measured without the presence of any protein. Examples of pH buffers that may be used include, but are not limited to, Tris, phosphate, acetate, citrate, formic acid, and ammonium buffers, as well as combinations of these. The preferred buffers are citrate, acetate, and formic acid buffers.

In some embodiments, the high point of the pH gradient ranges from pH 5.1 to 6.0 and the low point of the pH gradient ranges from pH 3.0 to 3.7.

In case of step elution as well as in case where a series of small pH change steps are use, two or more buffers are used sequentially in the order of descending pH values to create the steps. These buffers could be pre-made using similar buffers as described above or mixed with maintaining their pH using the chromatography system.

Without wishing to be bound by theory, it is contemplated that in some embodiments, the pH gradient elution method may be used in combination with the pH step elution method, e.g., one used after the other.

IV. Exemplary Ligands Used in the Methods Described Herein

The methods according to the present invention employ Protein A ligands based on the C domain of Protein A. In some embodiments, a ligand used in the methods described herein comprises the amino acid sequence set forth in SEQ ID NO:3. In other embodiments, a ligand used in the methods described herein comprises the amino acid sequence set forth in SEQ ID NO:4. Also encompassed by the present invention are variants, fragments and derivatives of these sequences, which bind an Fc-containing protein, as well as, when subjected to a pH gradient or pH step elution method, as described herein, result in the elution of at least 30% of protein aggregates prior to the elution of the Fc-containing protein.

V. Methods of Measuring the Level of Protein Aggregates in the Elution Pool Containing the Fc-containing Protein Proteins can aggregate or become misfolded. The desired target protein (i.e., monomer) is often co-purified with protein aggregates, when using affinity chromatography, e.g., Protein A chromatography. Accordingly, the protein aggregates often end up in the elution pool containing the target protein and the elution pool typically is subjected to one or more subsequent steps to remove such aggregates. Such additional steps may involve chromatography techniques which separate the aggregates on the basis of their charge, degree of hydrophobicity, or size. Exemplary techniques include, but not limited to, ion exchange chromatography, hydrophobic interaction chromatography, mixed mode chromatography, or size exclusion chromatography. These techniques typically remove protein aggregates after the Protein A step. However, each of these methods require additional buffers, resins or sorbents for further purification resulting in longer processing time and higher costs.

The methods described herein result in the removal of protein aggregates before and after the target protein during Protein A elution step, thereby increasing the overall product purity and either reducing the number of additional steps that are typically required to remove protein aggregates or obviate the need to use one or more additional steps.

As demonstrated herein, the level of protein aggregates in the elution pool containing the target protein is significantly lower relative to the methods described in the prior art, which only remove protein aggregates after the elution of the target protein. Consequently, the purity of the target protein in the elution pool is increased, as measured by the ratio of protein monomer versus total protein.

Protein aggregate levels can be measured in the various elution fractions using a number of methods known in the art and those described herein. For example, protein aggregates may be measured using dynamic light scattering, high pressure size exclusion chromatography, asymmetrical flow field flow fractionation, gel electrophoresis, fluorescence, or fluorescent dye detection.

Size exclusion chromatography is easily accessible and is often the tool of choice. Size exclusion chromatography separates species on the basis of molecular weight where the area under the UV chromatogram is used to quantify the relative amounts of monomeric, aggregate, and fragment species.

This invention is further illustrated by the following examples which should not be construed as limiting. The contents of all references, patents and published patent applications cited throughout this application, as well as the Figures, are incorporated herein by reference.

EXAMPLES

Example 1

Generation of Protein A Ligands

Synthetic genes encoding two Protein A ligands based on the C domain are obtained from DNA 2.0 (Menlo Park, Calif.). The amino acid sequences of these ligands are set forth in SEQ ID NO:3 and 4.

The 5' end of each synthetic gene includes a codon for an initiating methionine. The 5' and 3' ends of each gene contain NdeI and BamHI restriction sites, respectively. These synthetic genes as well as the expression vector that is used, i.e., pET11a, are digested with NdeI and BamHI (NEW ENGLAND BIOLABS, Ipswich, Mass.), the DNA fragments are separated on a 0.7% agarose TAE gel and the appropriate DNA fragments are excised and purified using the gel extraction kit from QIAGEN (Valencia, Calif.). The purified inserts are ligated into the backbone of a pET11a or any other suitable expression vector using T4 DNA ligase (NEW ENGLAND BIOLABS, Ipswich, Mass.).

The ligation reaction is transformed into DH5α competent *E. coli* (INVITROGEN, Carlsbad, Calif.), as per manufacturers instructions and plated on Technova LB plates containing 100 µg/mL ampicillin and grown overnight at 37° C. In order to obtain purified DNA, individual colonies are picked for overnight culture in LB containing 100 µg/mL ampicillin. DNA is purified using spin mini-prep kits from QIAGEN (Valencia, Calif.). The identity of recombinant plasmids is confirmed by restriction digest analysis using NdeI and BamHI (NEW ENGLAND BIOLABS, Ipswich, Mass.).

Example 2

Expression and Purification of the Protein A Ligands

The Protein A ligands described in Example 1 are expressed in an *Escherchia coli* strain such as strain BL21 (DE3) (PROMEGA, Madison Wis.) using a pET vector such as pET11a.

A single colony is selected from a plate and grown overnight at 37° C. in LB media containing 100 □g/mL, ampicillin. The overnight culture is diluted 100-fold into fresh LB media containing 100 □g/mL ampicillin and grown to a cell density such that the optical density at 600 nm is ~0.8. Following the addition of 1 mM isopropyl-beta-D-thiogalactopyranoside, cells are grown for an additional two hours. Expression is confirmed by SDS-PAGE analysis and Western blotting.

Cells are harvested by centrifugation (4000 rpm, 4° C., 5 minutes) and resuspended in 3 mL of phosphate buffered saline containing 20 mM imidazole. Cells are lysed by sonication, and cell debris is pelleted by centrifugation (4000 rpm, 4° C., 30 minutes). Protein A ligands are purified using a 50 mL IgG affinity resin (Polyclonal hIgG immobilized on controlled pore glass), applying ~500 mL cell lysate. Columns are washed with 30 mL phosphate buffered saline and the Protein A ligands are eluted in 0.1 M citric acid, pH 3. The ligands are dialyzed overnight into 18 mega-Ohm Milli-Q® water (EMD MILLIPORE, Billerica, Mass.). Protein concentration is confirmed using the UV spectrometer based on theoretical extinction coefficient (Pace et. al., Protein Science 4:2411 (1995)).

Example 3

Attachment of Protein A Ligands to a Solid Support

Subsequent to the generation and expression of various ligands, as described in Examples 1 and 2, they are immobilized via multipoint attachment to a solid support.

In an exemplary experiment, the Protein A ligand (SEQ ID NO: 3, 10 ~20 mg/mL) is immobilized onto a crosslinked polyvinyl alcohol base matrix described in U.S. Pat. No. 7,951,885, incorporated by reference herein, via the reaction of epoxy groups on the resin surface and the numerous amino groups on the ligand in the presence of 1~1.1 M $Na_2SO_4$ overnight. See, Hermanson et. al. Academic Press, 1992, page 118.

Method of coupling of ligand of SEQ NO:4 is similar to the process above.

Example 4

Generation of mAb Feed with Aggregates

Two different Fc-containing proteins, mAb-1 and mAb-2, are purified using a pH gradient elution method on different Protein A chromatography resins.

The mAb-1 and mAb-2 loading material is intentionally aggregated to facilitate an analysis of the different species in the elution pool. The generation of aggregates is accomplished using a previously developed method (see, e.g., ACS National Meeting 2012, Cataldo et al.). Specifically, a pH cycling method is used to produce non-reversible and solution stable aggregates. Purified mAb is concentrated using centrifugal filter devices (Amicon Ultra-15, 10,000 NMWL). The pH is raised to pH 11.0 using 10 and 1 N NaOH with gentle stirring and then allowed to sit for one hour at room temperature. Subsequently, the pH is lowered slowly (over approximately 20 minutes) to pH 5.0 using 6 and 1 M HCl with gentle stirring. This procedure is repeated 3 times and then the solution is filtered using a 0.22 µm syringe filter and dialyzed into the equilibration buffer prior to running the chromatography experiments.

Example 5 pH Gradient Elution Protein A Chromatography

Chromatography experiments are carried out on an AKTA Avant platform (GE Healthcare) controlled by Unicorn 6.1 software. Protein A colunmns are packed according to manufacturer's guidelines with MabSelect SuRe™ (GE Healthcare), ProSep® Ultra Plus (EMD Millipore), Resins A and B with ligand of SEQ ID NOs:3 and 4, respectively, and Resin C. Description of the various chromatography resins used in the Examples described herein is set forth in Table 1. Experiments are carried out using 0.66 cm (inner diameter)×14 cm (bed height) columns.

TABLE 1

Description of resins.

| Resins | Commercial Name | Base matrix | Protein A ligand |
|---|---|---|---|
| MabSelect SuRe ™ | MabSelect SuRe ™ (GE Healthcare) | Agarose | Engineered Z domain tetramer |
| ProSep ® Ultra Plus | ProSep ® Ultra Plus (EMD Millipore) | Controlled pore glass | rSPA (Recombinant full length Protein A) |
| Resin A | — | Polyvinyl alcohol | SEC ID NO. 3 |
| Resin B | — | Polyvinyl alcohol | SEC ID NO. 4 |
| Resin C | — | Polyvinyl alcohol | rSPA (Recombinant full length Protein A) |

A pH gradient is used for elution, whereby an Fc-containing protein is bound to a Protein A ligand at high pH and the pH is gradually lowered during elution. The Avant chromatography system produces this pH gradient by mixing two buffers in a changing proportion using a two pump system where the flow rate is maintained and the percent of the flow that each of the pumps delivers changes over time. The columns are equilibrated for 5 column volumes (CV) with the initial buffer of 0.1 M citric acid, pH 6.0. An Fc-containing protein (e.g., an antibody) is loaded onto the columns and then washed with the equilibration buffer for 4 CVs. The antibody is then eluted using a linear gradient where the buffer transitions to 0.1 M citric acid, pH 3.0 over 20 CVs. A gradient delay of 5 CVs is used.

Then, the columns are cleaned using 0.1 M sodium hydroxide (MabSelect SuRe™, Resin C, Resin A and Resin B) or 6 M guanidine HCl (ProSep® Ultra Plus). The columns are subsequently re-equilibrated. The flow rate is 1.6 mL/min (3 minute residence time) for all steps with the exception of the protein loading step which has a flow rate of 0.8 mL/min (6 minute residence time). Fractions are collected every 0.5 CV during the elution portion of each method. The antibody concentration in each fraction is determined using an Agilent 1100 series (Agilent Technologies) HPLC with a POROS® A/20 (Applied Biosystems) Protein A column of dimensions 2.1 mm×30 mm (ABI 1-5024-12, S/N 33504). These fractions are further characterized for high molecular weight (HMW) species which represent aggregates, using analytical assays described below. Experiments are also carried out at different loading densities ranging from 12 mg/mL of resin to 40 mg/mL of resin.

Example 6

Determination of High Molecular Weight Species in Elution Pool Using Size Exclusion Chromatography An Agilent 1260 Infinity series (Agilent Technologies) HPLC is used to carry out SEC experiments for determining the relative levels of high molecular weight (HMW) species, monomer, and low molecular weight (LMW) species in different samples. A TSKgel SuperSW3000 (TOSOH Biosciences, #08541) column of dimensions 3.6 mm (inner diameter)×30 cm (bed height) with 4 µm particle size is used along with a guard column (TOSOH Biosciences #08543). The buffer system used is 0.2 M sodium phosphate, pH 7.0 with a flow rate of 0.35 mL/min. Sample injections are adjusted such that approximately 10 µg of antibody is loaded per sample (injection volumes ranged from 1 to 100 µL). Blanks containing the background buffer are run with each sample set. Gel filtration standards (Bio-Rad 151-1901) are also analyzed to confirm column performance. HPLC chromatograms are monitored by UV absorbance at 230 nm and 280 nm. The absorbance curves are analyzed using Agilent ChemStation software for peak integration. Percent values obtained from this assay can be multiplied by the concentration (mg/mL) of the fraction to obtain actual concentration or mass for each size variant species in the sample (e.g., SEC result: 4% HMW, 92% monomer, 4% LMW species; sample concentration: 2 g/L; sample volume: 10 mL; 1.84 g/L monomer, 18.4 mg monomer total in sample). Chromatograms are aligned and normalized based on the monomer elution pool as shown in the sample overlays.

Figure 1B:
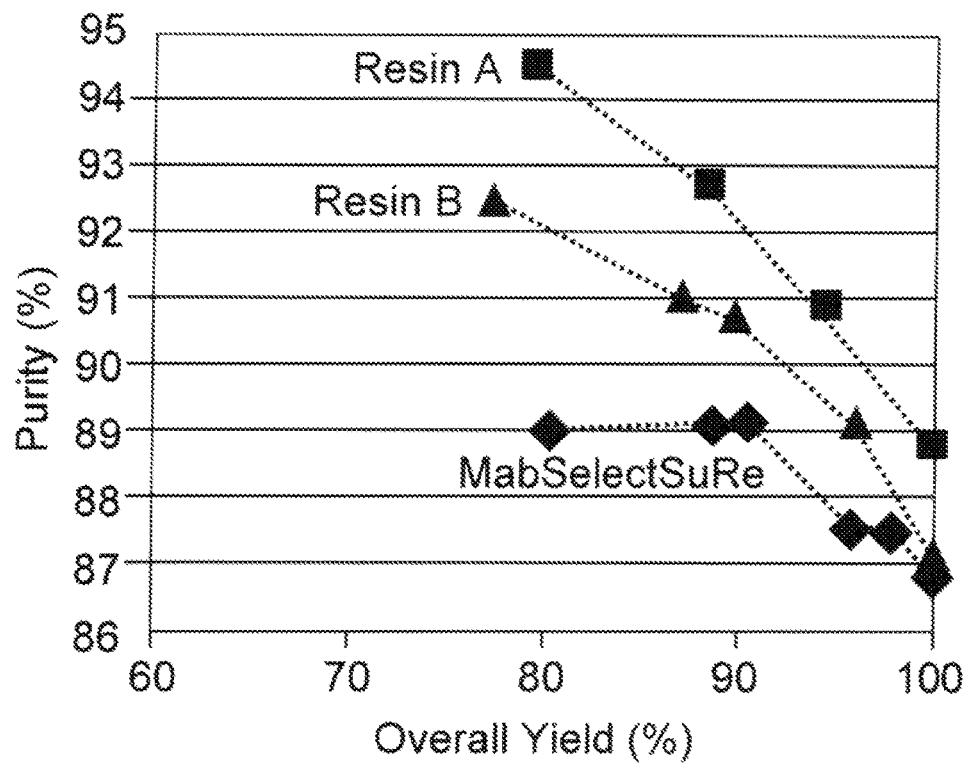
FIG. 1B depicts yield versus monomer purity for mAb-1 (loading density 12 mg/mL) using pH gradient elution from MabSelect SuRe™ (shown by diamonds), Resin A (shown by squares), and Resin B (shown by triangles). Resin A and Resin B achieve higher levels of monomer purity than MabSelect SuRe™ while maintaining high yields.

The UV trace of the elution portion of the chromatograms from the pH gradients with mAb-1 (loading density of 12 mg/mL) are shown in FIG. 1A by a solid line. The corresponding aggregate content obtained from SEC is shown by linked squares. The corresponding elution pool purity and yield data for cutting the peak at 500 mAU are shown in Table 2. FIG. 1B depicts the yield versus monomer purity for MabSelect Sure™ and Resins A and B.

SEC chromatograms of different fractions within the elution profile demonstrate that fractions from the beginning and end of the profile from Resins A and B contain a large percentage (higher than 30%) of total aggregate removed in the pre-peaks. After cutting the profile at 500 mAU, these aggregate species are removed, producing high purity levels in the resulting elution pool. Resin A and Resin B both demonstrate high elution pool purity, as summarized in Table 2. Table 2 contains the yield and purity data for mAb-1 pH gradient elution from three resins. The elution peaks are cut to include the portions which have UV 280 absorbance greater than 500 mAU. The purity in the pool is determined after cutting the peak and is calculated as the total amount of monomer in the pool as compared to the total protein amount in the pool. The overall yield is determined after cutting the peak and is calculated as the total amount of mAb in the elution pool relative to the total amount of protein recovered in the elution fractions from the entire elution profile.

TABLE 2

Yield and purity data for mAb-1 (loading density 12 mg/mL) pH gradient elution.

| Resin | Monomer in Pool (%) | Overall mAb Yield (%) | Pre-Peak % Aggregate Removed | Pre-Peak % of Total | Post-Peak % Aggregate Removed | Post-Peak % of Total | Total Aggregate Removed (%) |
|---|---|---|---|---|---|---|---|
| MabSelect SuRe ™ | 88.9 | 80.3 | 6.1 | 18.9 | 26.1 | 81.1 | 32.2 |
| Resin A | 94.6 | 79.4 | 25.7 | 41.1 | 36.9 | 58.9 | 62.6 |
| Resin B | 92.6 | 77.3 | 22.3 | 32.8 | 45.7 | 67.2 | 68.0 |

Figure 2:
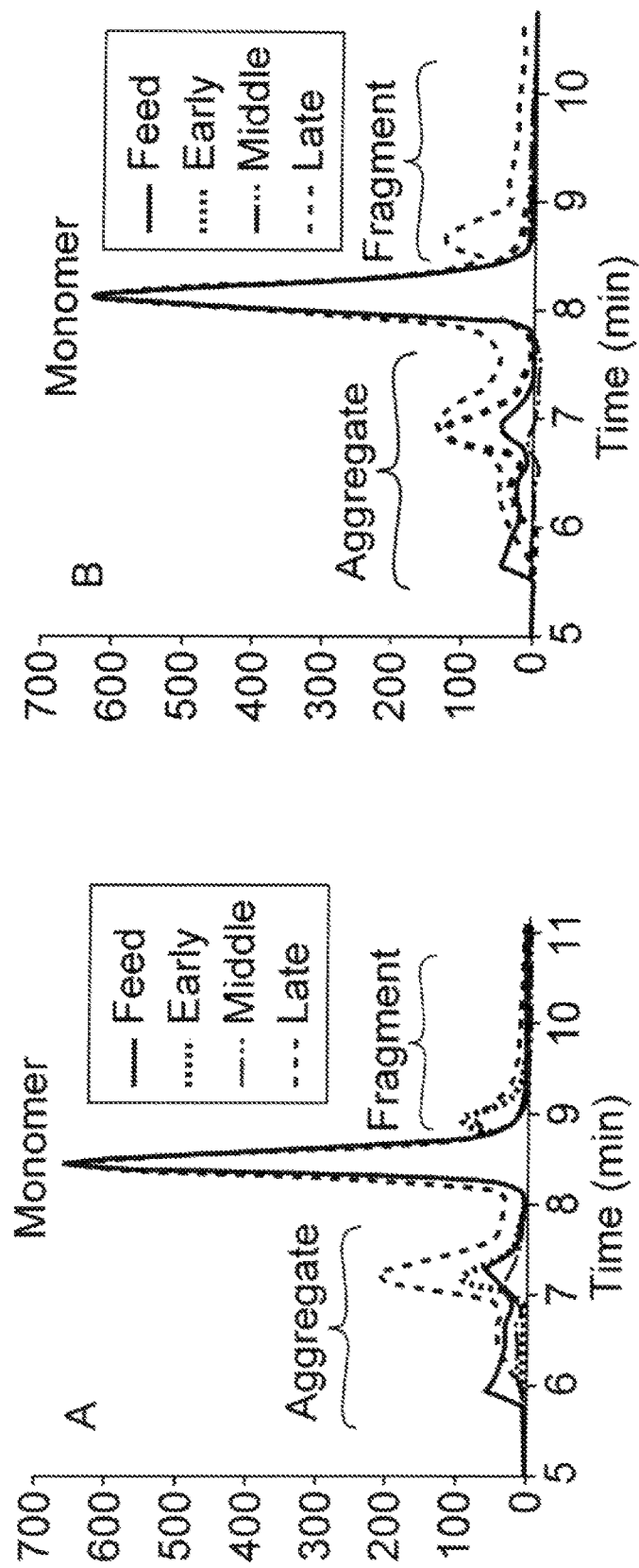
FIG. 2 shows representative SEC profiles obtained for MabSelect SuRe™ and Resin A elution fractions. The X-axis represents time and the Y-axis is UV absorbance at 280 nm. The feed profile is shown (shown by solid black line), as well as a fraction from the early part of the elution profile (pre-peak, shown by grey dashed line), the middle of the elution profile (shown by black dashed line), and the late part of the elution peak (post-peak, shown by dotted line). The peaks are normalized and aligned based on the monomer peak (8-9 minutes). For MabSelect SuRe™, a greater amount of aggregate removal is observed in the fractions eluting towards the end of the profile. For Resin A, a greater amount of aggregate removal is observed in the pre-peak and post-peak fractions.

Representative SEC chromatograms from the beginning, middle, and end of the elution profiles for MabSelect SuRe™ and Resin A are shown in FIG. 2. The profiles have been normalized and aligned based on the monomer peak (8-9 minutes). For MabSelect SuRe™, a large aggregate peak was observed in the fractions eluting towards the end of the profile. Whereas, for Resin A, a large aggregate peak was observed in both the early and late eluting fractions.

Figure 3:
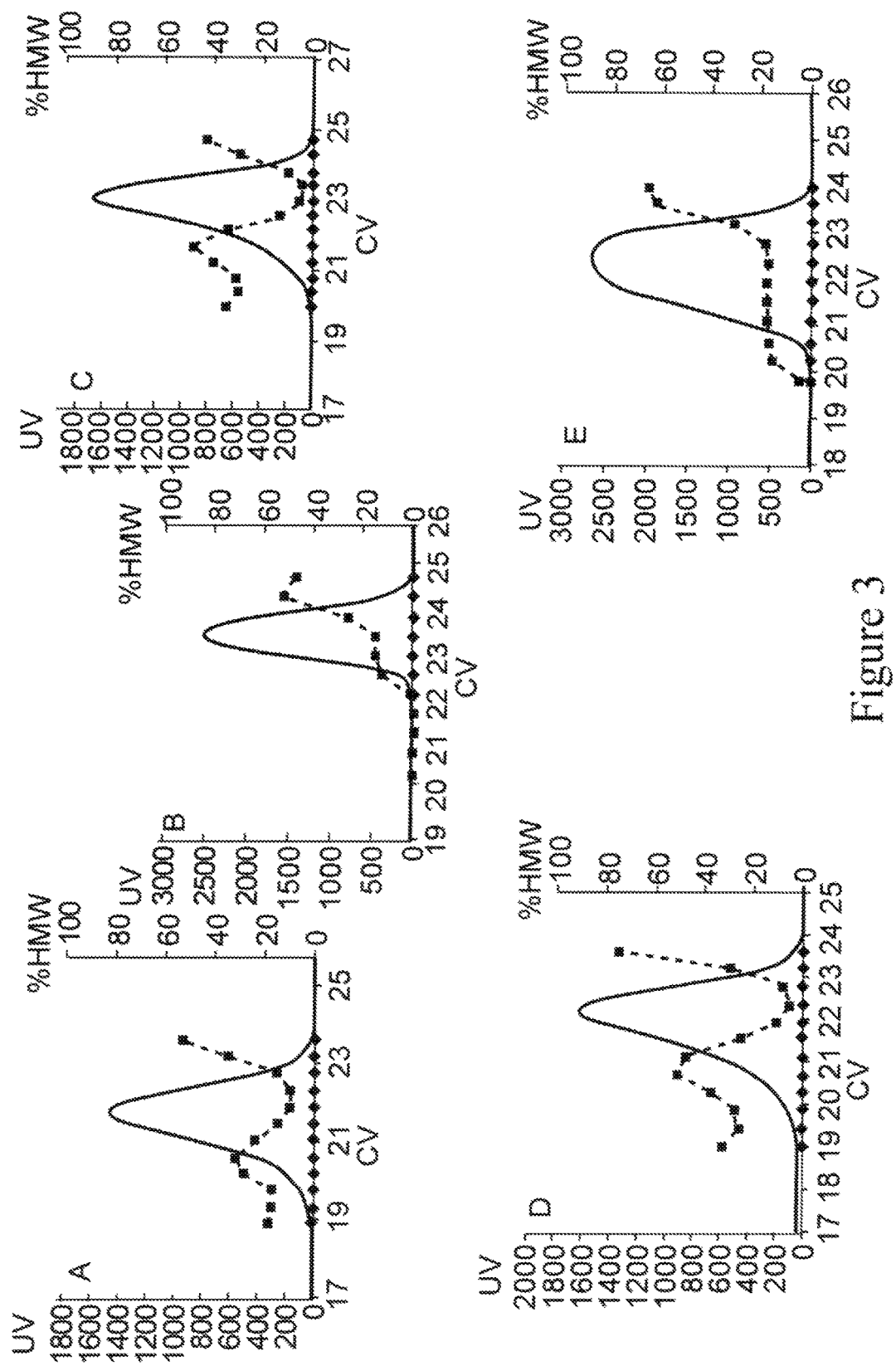
FIG. 3 depicts the elution region of chromatograms for mAb-2 (loading density 12 mg/mL) with pH gradient elution from five resins (A-MabSelect Sure™; B-ProSep® Ultra Plus; C-Resin A; D-Resin B; and E-Resin C), where the X-axis represents column volumes (CV), the left Y-axis is UV 280 absorbance (measured in mAU and shown by solid line), and the right Y-axis is the percentage of aggregate species in each fraction as determined by SEC (shown by linked squares). The amount of aggregates removed in the pre-peak for Resin A and Resin B is significantly higher than those for MabSelect SuRe™, ProSep® Ultra Plus, or Resin C.

FIG. 3 shows the UV trace of the relevant elution portion of the chromatograms from pH gradients with mAb-2 (loading density of 12 mg/mL). The corresponding aggregate content obtained from SEC is shown by linked squares. The corresponding elution pool purity and yield data for cutting the peak at 500 mAU are shown in Table 3. The results are similar to those obtained with mAb-1.

Table 3 contains the yield and purity data for mAb-2 pH gradient elution from five resins. The elution profiles were cut to include the portions which had UV 280 absorbance greater than 500 mAU. The purity in the pool is determined after cutting the profile and is calculated as the total amount of monomer in the pool as compared to the total protein in the pool. The overall yield is determined after cutting the peak and is calculated as the total amount in the pool as compared to the total amount recovered in the elution fractions from the entire elution profile.

The highest pool purity is obtained with Resin A. The fractions from the pre-peak and post-peak from Resins A and B contain a large percentage of HMW species. The SEC data for ProSep® Ultra Plus and Resin C indicated that aggregate species are predominantly in the tail portion of the elution profiles for these resins, as reported in the prior art. Resins A and B remove greater than 90% of the total aggregates removed in the pre-peaks, as summarized in Table 3 below.

Figure 4:
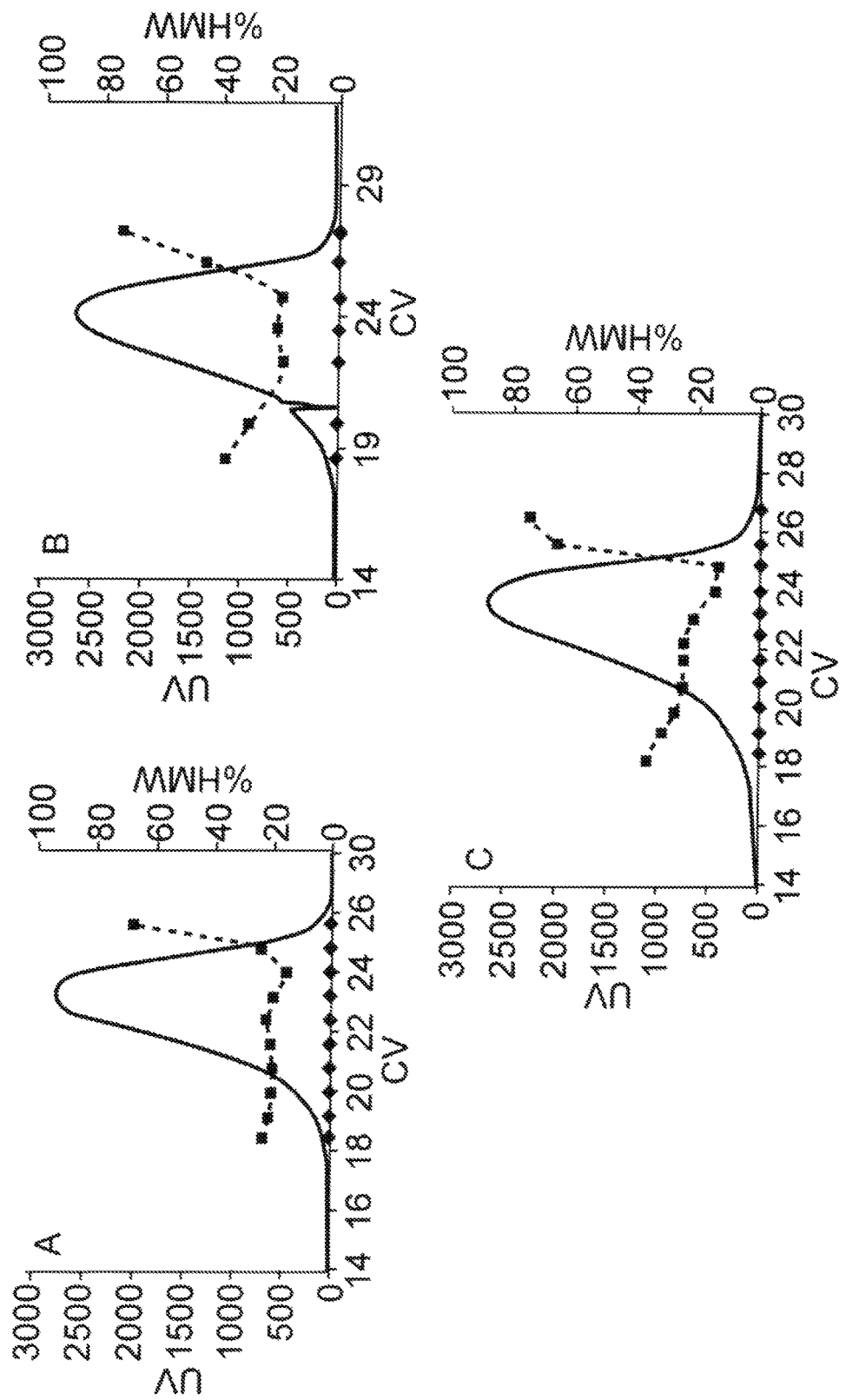
FIG. 4 depicts the elution region of chromatograms for mAb-2 (loading density 40 mg/mL) with pH gradient elution from three resins (A-MabSelect Sure™; B-Resin A and C-Resin C), where the X-axis represents column volumes (CVs), the left Y-axis is UV 280 absorbance (measured in mAU and shown by solid line), and the right Y-axis is the percentage of aggregate species in each fraction as determined by SEC (shown by linked squares).

FIG. 4 shows results obtained for higher loading densities, 40 mg per mL of resin. Similar to the lower loading density results in Table 2, Resins A and B show a large amount of aggregate species at the beginning and end of the elution profiles.

Table 4 shows the yield and purity data for mAb-2 pH gradient elution from three resins at 40 mg/mL loading densities. The elution profiles were cut to include the portions which had UV 280 absorbance greater than 500 mAU. The purity in the pool is determined after cutting the profile and is calculated as the total amount of monomer in the pool as compared to the total mass in the pool. The overall yield is determined after cutting the profile and is calculated as the total amount of protein in the pool as compared to the total amount recovered in the elution fractions from the entire elution profile. As shown below, Resins A and B remove greater than 48% of the total aggregates in this step in the pre-peaks.

TABLE 4

Yield and purity data for mAb-2 (loading density of 40 mg/mL) pH gradient elution.

| Resin | Monomer in Pool (%) | Overall mAb Yield (%) | Pre-Peak | | Post-Peak | | Total Aggregate Removed (%) |
| --- | --- | --- | --- | --- | --- | --- | --- |
| | | | % Aggregate Removed | % of Total | % Aggregate Removed | % of Total | |
| Resin A | 82.7 | 89.0 | 9.6 | 48.0 | 10.4 | 52.0 | 20.0 |
| Resin B | 81.7 | 91.7 | 10.3 | 70.1 | 4.4 | 29.9 | 14.7 |

Example 7

DH Step Elution for Protein A Chromatography

An Fc-containing protein, mAb-2, is purified using a pH step elution method, as described below.

Chromatography experiments are carried out on an AKTA Avant (GE Healthcare) controlled by Unicorn 6.1 software. Protein A columns are packed with MabSelect SuRe™, Resin A or Resin B. Experiments are carried out using 0.66 cm (inner diameter)×14 cm (bed height) columns. The columns were qualified using asymmetry testing.

A pH step is used for elution whereby the protein is bound at high pH and the pH is lowered in a stepwise manner

TABLE 3

Yield and purity data for mAb-2 (loading density 12 mg/mL) pH gradient elution.

| Resin | Monomer in Pool (%) | Overall mAb Yield (%) | Pre-Peak | | Post-Peak | | Total Aggregate Removed (%) |
| --- | --- | --- | --- | --- | --- | --- | --- |
| | | | % Aggregate Removed | % of Total | % Aggregate Removed | % of Total | |
| MabSelect SuRe ™ | 82.2 | 86.6 | 11.2 | 67.5 | 5.4 | 32.5 | 16.6 |
| ProSep ® Ultra Plus | 81.0 | 96.9 | 0 | 0 | 7.4 | 100 | 7.4 |
| Resin A | 86.6 | 82.2 | 40.5 | 97.6 | 1.0 | 2.4 | 41.5 |
| Resin B | 83.8 | 85.2 | 27.9 | 92.7 | 2.2 | 7.3 | 30.1 |
| Resin C | 81.1 | 98.5 | 0.7 | 23.3 | 2.3 | 76.7 | 3.0 | during elution. The Avant chromatography system produces this pH step by mixing two buffers in specified proportions using a two pump system. The columns are equilibrated at 0.1 M citric acid, pH 5. Antibody is loaded onto the columns and then washed with the equilibration buffer for 9 CVs. The method is programmed to mix the buffers to achieve a concentration of 0.1 M citric acid, pH 3.75 for 10 CVs, and then lowered to 0.1 M citric acid, pH 3 for 10 CVs. The columns are then cleaned using 0.1 M sodium hydroxide, followed by re-equilibration. The flow rate is set at 1.6 mL/min (3 minute residence time) for all steps with the exception of the protein loading step which had a flow rate of 0.8 mL/min (6 minute residence time). Fractions are collected every 1 CV during the elution portion of the method. These fractions are characterized using the analytical assays described above.

Figure 5:
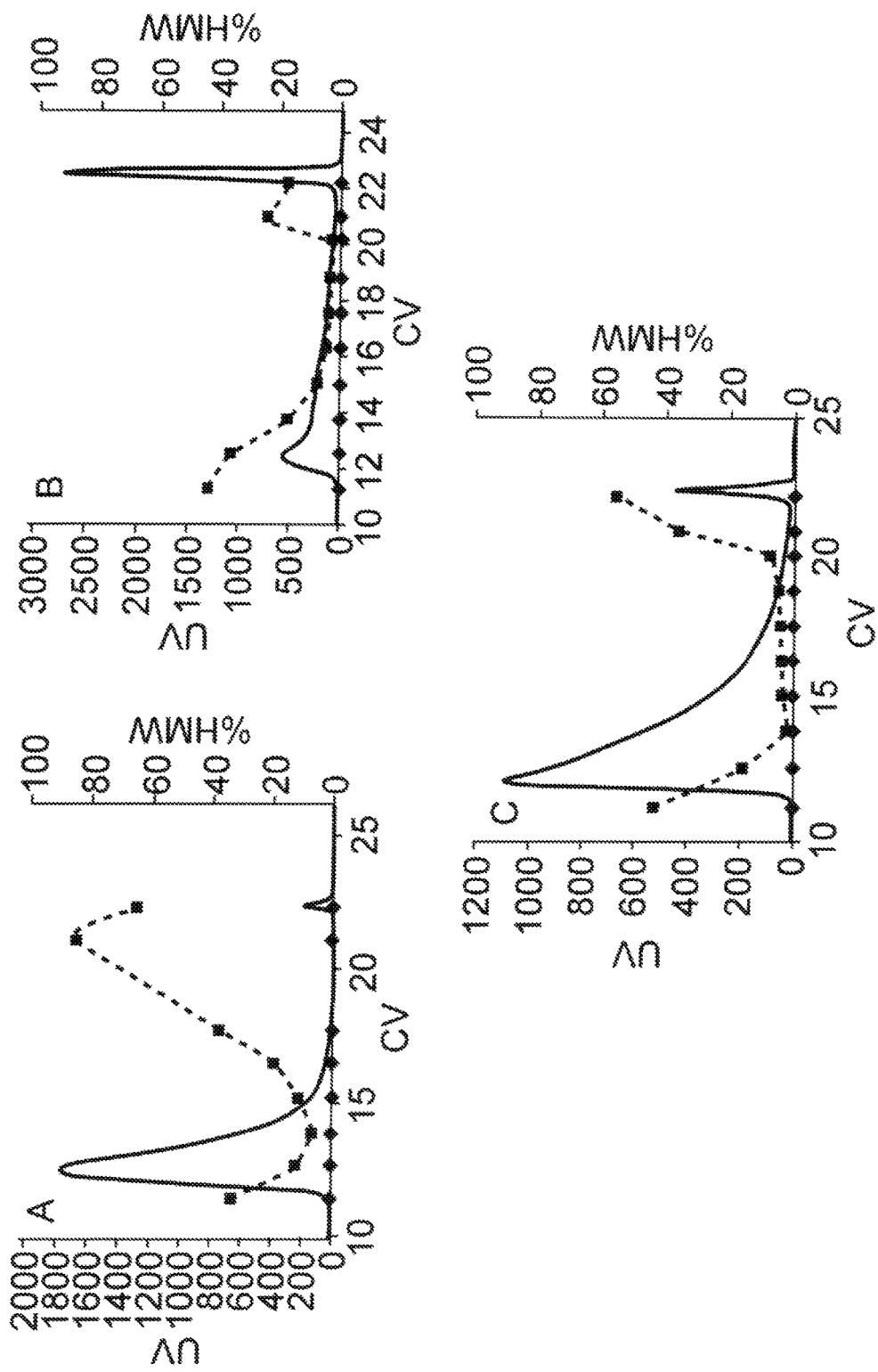
FIG. 5 depicts the elution region of chromatograms for mAb-2 (loading density 12 mg/mL) with pH step elution from three resins (A-MabSelect Sure™; B-Resin A and C-Resin C), where the X-axis represents column volumes (CVs), the left Y-axis is UV 280 absorbance (measured in mAU and shown by solid line), and the right Y-axis is the percentage of aggregate species in each fraction as determined by SEC (shown by linked squares).

The pH step elution results with mAb-2 are shown in FIG. 5. The corresponding elution pool purity and yield data based on cutting the profile to exclude the first two fractions are shown in Table 5. Table 5 contains the yield and purity data for mAb-2 pH step elution from three resins. The elution profiles are cut to exclude the first two fractions. The purity in the pool is determined after cutting the profile and is calculated as the total amount of monomer in the pool as compared to the total amount of protein in the pool. The overall yield is determined after cutting the profile and is calculated as the total amount in the pool as compared to the total amount recovered in the elution fractions from the entire elution profile.

Resin A provides the highest total mAb yield while also providing the highest monomer purity (88.3%). Resin B provides the highest monomer purity (92.1%) with moderate overall yield. This indicates that a pH step elution strategy can be useful in reducing aggregate levels in the final product pool.

TABLE 5

Yield and purity data for mAb-2 (loading density 12 mg/mL) pH step elution.

| Resin | Monomer in Pool (%) | Overall mAb Yield (%) |
|---|---|---|
| MabSelect SuRe ™ | 86.9 | 18.5 |
| Resin A | 88.3 | 69.9 |
| Resin B | 92.1 | 44.6 |

Example 8

Step Elution Employing a Series of Small pH Change Steps for Protein A Chromatography In this exemplary experiment, an Fc-containing protein, mAb-3, is purified using a series of small pH change steps, as described below.

Chromatography experiments are carried out on an AKTA Avant (GE Healthcare) controlled by Unicorn 6.1 software. Protein A columns are packed with Resin A. Experiments are carried out using 0.66 cm (inner diameter)×14 cm (bed height) columns. The columns are qualified using asymmetry testing.

A series of small pH change steps is used for elution, whereby the protein is bound at high pH and the pH is lowered in a stepwise manner during elution. The Avant chromatography system can produce this pH step by mixing two buffers in specified proportions using a two pump system. The antibody feed initially contains 10.5% aggregates. The protein A column is equilibrated at 0.1 M citric acid, pH 5 for 5 CVs. Antibody feed is loaded onto the columns and then washed with the equilibration buffer for 5 CVs. For elution of the antibody, the method is programmed to mix the 0.1 M citric acid, pH 5 buffer with 0.1 M citric acid, pH 3 buffer in order to obtain solutions at pH 5.0, 4.8, 4.6, 4.4, 4.2, 4.0, 3.8, 3.6, 3.4, 3.2, and 3.0. Each pH step is held for 3 CVs before moving to the next step. The columns are then cleaned using 0.1 M sodium hydroxide for 3 CVs, followed by re-equilibration with 0.1 M citric acid, pH 5 for 5 CVs. The flow rate is set at 1.6 mL/min (3 minute residence time) for all steps with the exception of the protein loading step which has a flow rate of 0.8 mL/min (6 minute residence time). Fractions are collected every CV during the elution portion of the method. These fractions are characterized using the analytical assays described above.

Figure 6:
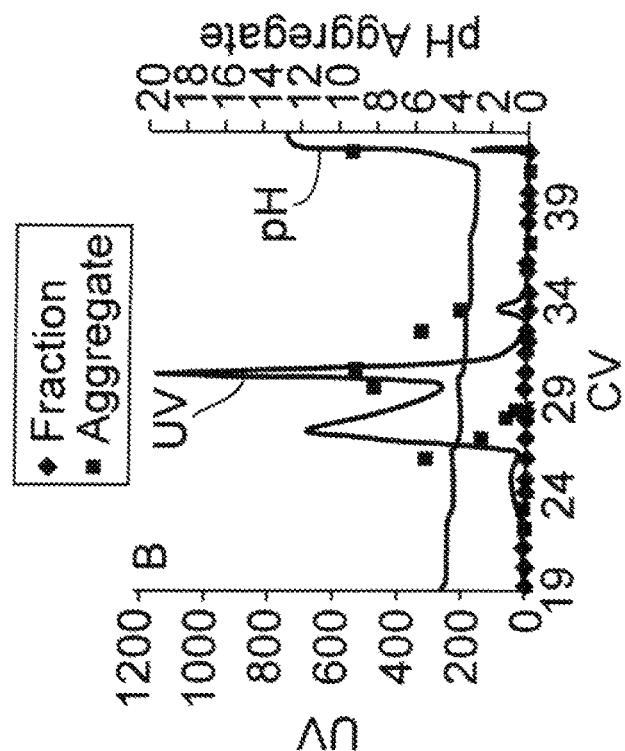
FIG. 6 depicts a chromatogram for mAb-3 using Resin A employing a series of small pH change steps for elution, with each pH step differing from the previous pH step by a value of 0.2.
Figure 6:
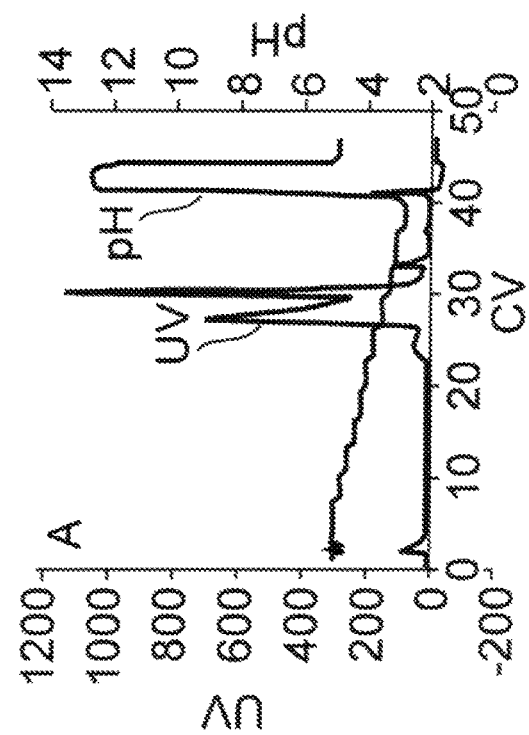

The small pH step elution results with mAb-3 are shown in FIG. 6. The purity and yield levels depend on which fractions of the elution peak are selected for pooling. Several scenarios are shown in Table 6. While higher purity levels can be achieved by pooling only the high purity fractions, this may adversely affect the yield. Nearly full recovery of the antibody is achieved when fractions from 22-34 CVs are pooled. The resulting purity is 93%. By selecting only fractions containing high purity, it is possible to improve the purity of the pool. A purity level of 95% is achieved when fractions from 26-29 CV are pooled, resulting in a yield of about 70%. The purity level is about 96% when pooling fractions from 27-29 CVs, resulting in a yield of about 57%. The purity in the pool is determined after pooling the desired fractions and is calculated as the total amount of monomer in the pool as compared to the total amount of protein in the pool. The overall yield is determined after pooling the fractions and is calculated as the total amount in the pool as compared to the total amount recovered in the elution fractions from the entire elution profile.

TABLE 6

Yield and purity data for mAb-3 small pH step elution from Resin A. The initial feed monomer purity is 89.5%.

| CVs Pooled | Monomer in Pool (%) | Overall mAb Yield (%) |
|---|---|---|
| 22-34 | 92.9 | 99.8 |
| 26-32 | 93.5 | 89.7 |
| 26-29 | 95.2 | 70.0 |
| 27-29 | 96.0 | 57.1 |

This indicates that a series of small pH change steps can be useful in reducing aggregate levels in the final product pool from Resin A. By using small pH change steps, it is possible to identify the desired pH cutoff levels in order to optimize purity and yield. This approach can be used to guide the development of a simplified pH step elution process, as described above in Example 7. The simplified process may contain fewer pH step changes, which are strategically selected in order to optimize purity and yield for a given process.

The specification is most thoroughly understood in light of the teachings of the references cited within the specification which are hereby incorporated by reference. The embodiments within the specification provide an illustration of embodiments in this invention and should not be construed to limit its scope. The skilled artisan readily recognizes that many other embodiments are encompassed by this invention. All publications and inventions are incorporated by reference in their entirety. To the extent that the material incorporated by reference contradicts or is inconsistent with the present specification, the present specification will supercede any such material. The citation of any references herein is not an admission that such references are prior art to the present invention.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

What is claimed is:

1. A method of reducing the level of protein aggregates in an elution pool containing an Fc-containing protein, the method comprising the steps of:
   (a) providing a sample comprising an Fc-containing protein and protein aggregates;
   (b) contacting the sample with a protein A ligand immobilized onto a solid support, wherein the protein A ligand consists of one or more C-based domains of Protein A, such that the Fc-region containing protein binds to the protein A ligand;
   (c) obtaining an elution pool containing the Fc-containing protein using a pH gradient method employing a high pH buffer and a low pH buffer;
   wherein at least 30% of the protein aggregates are removed prior to the elution of the Fc-containing protein in addition to protein aggregates that are removed after the elution of the Fc-containing protein, thereby reducing the level of protein aggregates in the elution pool.

2. A method of reducing the level of protein aggregates in an elution pool containing an Fc-containing protein, the method comprising the steps of:
   (d) providing a sample comprising an Fc-containing protein and protein aggregates;
   (e) contacting the sample with a protein A ligand immobilized onto a solid support, wherein the protein A ligand consists of one or more C-based domains of Protein A, such that the Fc-region containing protein binds to the protein A ligand;
   (f) obtaining an elution pool containing the Fc-containing protein using a pH step method employing two or more buffers used sequentially in the order of descending pH values,
   wherein at least 30% of the protein aggregates are removed prior to the elution of the Fc-containing protein in addition to protein aggregates that are removed after the elution of the Fc-containing protein, thereby reducing the level of protein aggregates in the elution pool.

3. The method of claim 2, wherein step (f) comprises two or more, or three or more, or four or more, or five or more, or six or more, or seven or more, or eight or more, or nine or more, or ten or more small pH change steps, with pH ranging from about 5.0 to about 3.0.

4. The method of claim 1, wherein high pH buffer has a pH of about 6.0 and the low pH buffer has a pH of about 3.0.

5. The method of claim 2, wherein at least one of the buffers used in the step elution method has a pH ranging from 3.6 to 4.4.

6. The method of claim 1, wherein the Fc-containing protein is selected from the group consisting of an antibody and an Fc-fusion protein.

7. The method of claim 2, wherein the Fc-containing protein is an antibody.

8. The method of claim 7, wherein the antibody is a monoclonal antibody.

9. The method of claim 2, wherein the Fc-containing protein is selected from the group consisting of an antibody and an Fc-fusion protein.

10. The method of claim 9, wherein the antibody is a monoclonal antibody.

11. The method of claim 1, wherein the pH gradient spans 5 column volumes to 30 column volumes.

12. The method of claim 1, wherein the solid support is selected from the group consisting of solid support is selected from the group consisting of controlled pore glass, silica, zirconium oxide, titanium oxide, agarose, polymethacrylate, polyacrylate, polyacrylamide, polyvinylether, polyvinyl alcohol and polystyrene and derivatives thereof.

13. The method of claim 2, wherein the solid support is selected from the group consisting of solid support is selected from the group consisting of controlled pore glass, silica, zirconium oxide, titanium oxide, agarose, polymethacrylate, polyacrylate, polyacrylamide, polyvinylether, polyvinyl alcohol and polystyrene and derivatives thereof.

14. The method of claim 1, wherein the Protein A ligand comprises the amino acid sequence set forth in SEQ ID NO:3 or SEQ ID NO:4.

15. The method of claim 2, wherein the Protein A ligand comprises the amino acid sequence set forth in SEQ ID NO:3 or SEQ ID NO:4.

16. The method of claim 1, wherein the solid support is polyvinyl alcohol or polyvinylether.

17. The method of claim 2, wherein the solid support is polyvinyl alcohol or polyvinylether.

18. A method of eluting Fc-containing protein aggregates before elution of Fc-containing monomer protein from an affinity ligand, the method comprising:
   (a) contacting a sample comprising a mixture of Fc-containing protein aggregates and an Fc-containing protein with an affinity ligand immobilized on a solid support, the affinity ligand consisting of one or more C-based domains of Protein A and which binds Fc-containing protein and Fc-containing protein aggregates;
   (b) applying a pH gradient elution buffer from a high pH to a low pH, thereby eluting at least 20% of aggregates from the mixture of aggregates and monomer bound to the affinity ligand on the solid support before elution of Fc-containing monomer protein from the affinity ligand.

19. The method of claim 18, wherein the high pH is about 6.0 and the low pH is about 3.0.

20. A method of eluting Fc-containing protein aggregates before elution of Fc-containing monomer protein from an affinity ligand, the method comprising:
   (a) contacting a sample comprising a mixture of Fc-containing protein aggregates and an Fc-containing protein with an affinity ligand immobilized on a solid support, the affinity ligand consisting of one or more C-based domains of Protein A and which binds Fc-containing protein and Fc-containing protein aggregates;
   (b) applying a pH step elution using two or more buffers with sequentially descending pH values from a high pH to a low pH, thereby eluting at least 20% of aggregates from the mixture of aggregates and monomer bound to the affinity ligand on the solid support before elution of Fc-containing monomer protein from the affinity ligand.

21. The method of claim 20, wherein the pH step elution comprises two, three, four, five, six, seven, eight, nine, ten or more step changes, wherein the pH step elution results in a pH change from between about pH 5.0 to about 3.0.

* * * * *